(12) United States Patent
Sato et al.

(10) Patent No.: US 6,569,809 B1
(45) Date of Patent: May 27, 2003

(54) PACKAGE-MIX AGRICULTURAL CHEMICAL COMPOSITIONS HAVING IMPROVED STABILITY

(75) Inventors: Tatsuo Sato, Tokyo (JP); Masus Kuchikata, Ibaraki (JP)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 09/671,785

(22) Filed: Sep. 27, 2000

(30) Foreign Application Priority Data

Sep. 30, 1999 (JP) .......................... 11-280132

(51) Int. Cl.$^7$ .................. A01N 25/04; A01N 25/26
(52) U.S. Cl. ................ 504/127; 504/128; 504/362; 504/363; 514/938; 514/963
(58) Field of Search ................. 504/127, 128, 504/362, 363; 514/938, 963

(56) References Cited

U.S. PATENT DOCUMENTS

| | | |
|---|---|---|
| 3,799,758 A | 3/1974 | Franz .......................... 71/86 |
| 3,853,530 A | 12/1974 | Franz .......................... 71/76 |
| 4,140,513 A | 2/1979 | Prill ............................. 71/86 |
| 4,315,765 A | 2/1982 | Large .......................... 71/87 |
| 4,405,531 A | 9/1983 | Franz ...................... 260/501.12 |
| 4,481,026 A | 11/1984 | Prisbylla ..................... 71/86 |
| 4,507,250 A | 3/1985 | Bakel ................... 260/502.5 F |
| 4,640,707 A | 2/1987 | Nagano et al. ............... 71/96 |
| 4,994,102 A | 2/1991 | Yoshido et al. ............... 71/86 |
| 6,127,318 A * | 10/2000 | Sato et al. ................... 504/128 |
| 6,165,939 A * | 12/2000 | Agbaje et al. ............... 504/105 |
| 6,313,070 B1 | 11/2001 | Bratz et al. |

FOREIGN PATENT DOCUMENTS

| | | |
|---|---|---|
| DE | 198 04 913 A1 | 8/1999 |
| GB | 1 302 795 | 1/1973 |
| WO | WO93/17554 | 9/1993 |
| WO | WO 98/17108 | 4/1998 |

OTHER PUBLICATIONS

PCT International Search Report, Feb. 12, 2001.

Tadros, "Disperse Systems in Pesticidal Formulations." Advances in Colloid and Interface Science, 1990, pp. 205–234, vol. 32, Elsevier Science Publishers B.V., Amsterdam.

* cited by examiner

*Primary Examiner*—S. Mark Clardy
(74) *Attorney, Agent, or Firm*—Senniger, Powers, Leavitt & Roedel; Joseph A. Schaper

(57) ABSTRACT

A concentrate package-mix composition comprising a water-soluble pesticide or plant growth regulator, for example a salt of the herbicide glyphosate, and a solid water-insoluble pesticide or plant growth regulator, for example the herbicide flumioxazin, is provided. The water-soluble pesticide or plant growth regulator is dissolved in a continuous aqueous phase of the composition and solid particles of the water-insoluble pesticide or plant growth regulator are suspended in the aqueous phase. These solid particles, individually or plurally, are intimately surrounded by a barrier layer, which comprises either one or both of a water-immiscible organic solvent or an emulsifying agent that has a hydrophile-lipophile balance (HLB) not greater than about 15. Optionally the composition further comprises a viscosity modifying agent, such as colloidal hydrophilic silica, dispersed in the aqueous phase. Compositions of the invention exhibit enhanced resistance to settling of the solid particles and/or enhanced resistance to chemical degradation of the water-insoluble pesticide or plant growth regulator by comparison with otherwise similar compositions lacking the barrier layer or the organic solvent.

43 Claims, No Drawings

PACKAGE-MIX AGRICULTURAL CHEMICAL COMPOSITIONS HAVING IMPROVED STABILITY

FIELD OF THE INVENTION

The present invention relates to pesticidal and/or plant growth regulating compositions useful in agriculture and related industries. More specifically, the present invention relates to liquid concentrate compositions containing at least two active ingredients. One of the active ingredients is water-soluble and the other is substantially water-insoluble. The liquid concentrate composition is suitable, following dilution in water, for application to plants or to soil. Active ingredients that can be formulated in compositions of the invention include pesticides, for example herbicides, algicides, fungicides, bactericides, viricides, insecticides, acaricides, nematicides and molluscicides, and plant growth regulators.

BACKGROUND OF THE INVENTION

For many purposes in agriculture and related endeavors it is desired to apply simultaneously two or more biologically active compounds, each of which is a pesticide or plant growth regulator, to the same locus. This is best accomplished by including the two or more compounds in a single composition which is applied, for example by spraying, to target plants or soil. Frequently such a composition is prepared by the user in the field by adding measured amounts of two or more concentrate compositions of the individual active ingredients to water in a spray tank, sometimes together with other ingredients. A composition prepared in this way is often known as a "tank-mix".

More conveniently, however, a single concentrate composition containing the two or more biologically active compounds, together with other ingredients if necessary or desirable, is provided to the user, who simply dilutes this composition in water prior to application. Such a composition is often known as a "package-mix". Package-mix compositions have many advantages, including reduced handling, reduced risk of dosage error, reduced packaging, etc. Package-mix compositions can take the form of solid materials such as powders or granules, but for many purposes liquid compositions are preferred.

A liquid concentrate package-mix composition of two active ingredients can be useful in a wide variety of applications, depending on the utility of the individual active ingredients. For example, it may be desired to simultaneously apply two insecticidal, fungicidal or herbicidal active ingredients in order to kill or control a wider spectrum of insect, fungal or weed species than can be killed or controlled with either one of the active ingredients alone. Alternatively, it may be desired to simultaneously apply two active ingredients having different modes of action or target sites, for example a contact herbicide and a systemic herbicide, to obtain improved effectiveness on a single species. Many other situations can readily be envisaged where a package-mix of two active ingredients is useful.

While effectiveness for the intended purpose is an important property determining the usefulness of a liquid concentrate package-mix composition, another very important property is storage stability of the composition. Chemical instability can sometimes be an issue but more commonly the primary issue is physical instability, manifested for example as phase separation, crystallization of an active or inert ingredient, settling or sedimentation of a particulate component, gelling, agglomeration, etc. Stability problems often do not become apparent immediately upon preparation of a composition, but instead are time-related. What constitutes an acceptable shelf-life for a particular product depends upon the product in question and the use to which it is put. In some cases a shelf-life of a few weeks or months is adequate, but more commonly an agricultural product is expected to remain stable under typical storage conditions for a minimum of one to two years. A product that is stable when stored for up to two years at temperatures of, say, 15° C. to 25° C. may relatively quickly exhibit instability problems if exposed to much higher temperatures, for example 50° C. to 60° C., or in a temperature cycling regime in which low temperatures (for example −10° C. to 0° C.) and higher temperatures (for example 25° C. to 35° C.) alternate.

Where both active ingredients are readily water-soluble or where both are water-insoluble, formulation of a storage-stable concentrate package-mix composition is generally fairly straightforward. However, where it is desired to provide a liquid package-mix composition of a water-soluble active ingredient with a water-insoluble active ingredient, in particular a solid (i.e., high melting point) water-insoluble active ingredient, formulation is much more difficult. This is because such a composition must be a two-phase or multiphase system, wherein the water-soluble compound is typically dissolved in an aqueous phase and the solid water-insoluble compound is typically either dispersed in the composition as a particulate phase, forming a suspension, or dissolved in an oil phase, the oil phase and aqueous phase together forming an emulsion. Although much teaching is available in the literature on stabilization of colloidal systems such as suspensions and emulsions, there remains a need for improved formulation technology where a physically and chemically stable liquid concentrate composition is desired containing a water-soluble pesticide or plant growth regulator and a solid water-insoluble pesticide or plant growth regulator.

In considering options for such a composition, an appropriate starting point is the formulation type known as a suspension concentrate (SC), wherein a finely particulate solid water-insoluble active ingredient is dispersed in a continuous aqueous phase having dissolved therein a water-soluble active ingredient. Tadros, Th. F. (1990) in a review article 'Disperse systems in pesticidal formulations', *Advances in Colloid and Interface Science*, 32, 205–234, summarized the main requirements for formulating an SC, namely the choice of dispersing agents and the choice of an anti-settling system.

According to Tadros, nonionic polymers and polyelectrolytes are the most preferred dispersing agents for SC formulations. Nonionic surfactants of the ethoxylate type are said to be adequate, provided they have enough ethylene oxide units to promote steric stabilization. Ionic surfactants are said to be the least attractive dispersing agents.

The anti-settling system most favored by Tadros for SC formulations is a "thickener" in the form of a viscosity modifying agent. Typical examples given are high molecular weight polymers such as hydroxyethyl cellulose or xanthan gum, or finely divided particulate materials such as bentonite or colloidal silica.

Suspoemulsions are a relatively recent development in pesticide formulation technology. These generally consist of a continuous aqueous phase in which two discontinuous phases are dispersed. One of the discontinuous phases is an oil phase and the other is a solid particulate phase. A suspoemulsion is therefore a mixture of a suspension and an oil-in-water emulsion. Tadros, in the above-cited review article, indicates that where both the oil phase and the solid particles can be dispersed using one surfactant and where the solid particles are insoluble in the oil phase, the general principles of stabilization of suspensions and emulsions can be applied also to suspoemulsions. Suspoemulsions are commonly considered in the art where it is desired to formulate a water-based concentrate package-mix composition of two water-insoluble active ingredients, one of which is liquid or readily soluble in oil and one of which is solid and relatively oil-insoluble.

Illustrative of the problems faced by the formulator desiring to prepare a liquid concentrate package-mix composition of a water-soluble active ingredient and a solid water-insoluble active ingredient are the particular problems faced where the water-soluble active ingredient is a salt of the herbicide N-phosphonomethylglycine (glyphosate) and the solid water-insoluble active ingredient is the herbicide 2-[7-fluoro-3,4-dihydro-3-oxo-4-(2-propynyl)-2H-1,4-benzoxazin-6-yl]-4,5,6,7-tetrahydro-1H-isoindole-1,3(2H)-dione (flumioxazin).

It would be of great benefit to a weed control practitioner to have a package-mix composition of these two herbicides. Glyphosate is a highly effective broad-spectrum herbicide that, through its systemic action in plants, kills roots as well as shoots and thereby provides total control without the regrowth commonly seen following treatment with non-systemic herbicides. However, a disadvantage is that symptoms of glyphosate phytotoxicity are slow to become visible in treated plants. Another disadvantage is that to control certain dicotyledonous weed species a high rate of glyphosate is required.

Tank-mix studies have shown that addition of a relatively small amount of flumioxazin to glyphosate alleviates both the above-mentioned disadvantages. Data from a tank-mix study in a greenhouse illustrating the benefit of simultaneous application of glyphosate+flumioxazin over a higher rate of glyphosate alone are presented in Table 1. Herbicide rates are given in grams per hectare (g/ha); rates shown for glyphosate (which was applied in this study as the isopropylammonium salt) are expressed as acid equivalent (a.e.). Herbicidal effectiveness is measured as percent inhibition by comparison with untreated plants, based on visual assessment by a technician trained in the art of making such assessments, at four times, namely 3, 7, 20 and 27 days after treatment (DAT). Data are presented for two dicotyledonous weed species, "inutade" (*Polygonum longisetum*) and "tsuyukusa" (*Commelina communis*), that are known to tolerate high rates of glyphosate.

TABLE 1

Herbicidal effectiveness of glyphosate-flumioxazin mixtures by comparison with glyphosate alone

| | | percent inhibition weed species: | | | | | | | |
|---|---|---|---|---|---|---|---|---|---|
| | | inutade | | | | tsuyukusa | | | |
| glyphosate | flumioxazin | DAT: | | | | | | | |
| g a.e./ha | g/ha | 3 | 7 | 20 | 27 | 3 | 7 | 20 | 27 |
| 2160 | 0 | 0 | 0 | 45 | 70 | 0 | 0 | 50 | 62 |
| 1460 | 75 | 5 | 18 | 77 | 99 | 10 | 34 | 89 | 100 |
| 1460 | 108 | 5 | 24 | 77 | 96 | 8 | 39 | 84 | 100 |

It will be noted from Table 1 that whereas glyphosate alone provided no visible symptoms of phytotoxicity up to 7 days after treatment, the addition of flumioxazin enabled symptoms to be visible as early as 3 days after treatment. Furthermore, control of both species was improved by addition of flumioxazin, even when the rate of glyphosate was reduced from 2160 to 1460 g a.e./ha.

U.S. Pat. No. 4,994,102 to Yoshido et al. discloses that glyphosate and flumioxazin applied together provide greater herbicidal effect than either compound applied alone, and that in combination the individual compounds can be used at lower rates than when used alone.

Thus a package-mix composition containing a glyphosate salt and flumioxazin would be a desirable product. However, two problems have to be overcome if such a package-mix composition is to be provided in a liquid form.

The first of these problems is physical instability of a suspension of flumioxazin particles in an aqueous solution of a glyphosate salt, and in particular the tendency of such a suspension to settle, because of the high specific gravity (1.51 at 20° C.) of flumioxazin.

The second problem is that flumioxazin has been found to undergo chemical degradation when exposed to a concentrated aqueous salt solution such as a solution of glyphosate salt for prolonged periods.

These problems, illustrative of similar problems facing the formulator of other active ingredients, have now surprisingly been overcome by the invention described below, which provides a novel approach to formulating a water-soluble pesticide or plant growth regulator and a solid water-insoluble pesticide or plant growth regulator, as illustrated by the herbicides glyphosate, in the form of a water-soluble salt thereof, and flumioxazin, respectively.

SUMMARY OF THE INVENTION

There is now provided a pesticidal and/or plant growth regulating concentrate composition comprising a continuous aqueous phase. Dissolved in the aqueous phase is a water-soluble active ingredient that is a pesticide or plant growth regulator. Suspended in the aqueous phase are solid particles of a substantially water-insoluble active ingredient that is a pesticide or plant growth regulator. These solid particles, individually or plurally, are intimately surrounded by a barrier layer, which comprises either one or both of a water-immiscible organic solvent and an emulsifying agent that has a hydrophile-lipophile balance (HLB) not greater than about 15.

Preferably the composition further comprises a viscosity modifying agent, such as colloidal hydrophilic silica, dispersed in the aqueous phase. It is preferred that the barrier layer comprise an organic solvent in which the substantially water-insoluble active ingredient is no more than sparingly soluble.

In one embodiment of the invention, the water-soluble active ingredient in a contemplated composition is an agriculturally acceptable salt of a herbicide and the substantially water-insoluble active ingredient is also a herbicide. In a particular embodiment, the substantially water-insoluble active ingredient exhibits chemical degradation when in direct contact with an aqueous solution of the water-soluble active ingredient.

In a further embodiment of the invention, the water-soluble active ingredient is an agriculturally acceptable salt of the herbicide N-phosphonomethylglycine and the substantially water-insoluble active ingredient is the herbicide flumioxazin.

A composition of the invention can be made by various processes. In an illustrative process a first premix is prepared by mixing with agitation a solid particulate substantially water-insoluble active ingredient that is a pesticide or plant growth regulator and either one or both of a substantially water-immiscible organic solvent and an emulsifying agent that has an HLB not greater than about 15, and a second premix is prepared by dissolving in water a water-soluble active ingredient that is a pesticide or plant growth regulator. A first portion of the second premix is added with agitation to the first premix, optionally followed by addition of a viscosity modifying agent, then the remaining portion of the second premix is added with agitation to form the finished composition.

A method of use of a composition of the invention is provided for eliciting a biological effect, such as a herbicidal effect, in a plant, by diluting the composition in a suitable volume of water and applying a biologically effective amount of the diluted composition, for example by spraying, to a locus such as soil or foliage from which active ingredients contained in the composition can enter the plant.

A contemplated composition exhibits at least one of the following benefits: (1) enhanced resistance to settling of solid particles; (2) enhanced resistance to chemical degradation of the substantially water-insoluble active ingredient. Such benefits are observable by comparison with an otherwise similar composition lacking only the barrier layer or the organic solvent component thereof.

These and other benefits will be evident from the detailed description that follows.

DETAILED DESCRIPTION OF THE INVENTION

Liquid concentrate compositions of the invention provide a new approach to making package-mix pesticide and/or plant growth regulator products and represent a new type of agricultural chemical formulation. This new type of formulation has characteristics of a suspension concentrate (SC), differing from SC formulations of water-insoluble active ingredients known in the art by the presence of a barrier layer intimately surrounding the suspended solid particles of the water-insoluble active ingredient. As the barrier layer has features similar to a discontinuous oil phase, the new type of formulation also has characteristics of a suspoemulsion (SE). However, compositions of the invention differ from SE formulations known in the art by having the suspended particles located in what can be considered the discontinuous oil phase rather than having the suspended particle phase and the emulsified oil phase independently dispersed in the continuous aqueous phase.

The barrier layer is an essential feature of compositions of the invention. It is believed, without being bound by theory, that by substantially preventing direct contact between the solid particles of the water-insoluble active ingredient and the aqueous phase, the barrier layer enhances physical stability of the composition as well as chemical stability of the water-insoluble active ingredient, in the case where the water-insoluble active ingredient exhibits chemical degradation in contact with an aqueous solution of the water-soluble active ingredient. Again without being bound by theory, it is believed that by providing an oil-water interface rather than a solid particle-water interface, the problems of physical stabilization become essentially those of a water-in-oil emulsion rather than those of a suspension. To the extent that emulsification problems are less intractable than suspension problems, an important new option is therefore provided to the formulator of pesticides and/or plant growth regulators.

It can be hypothesized that a barrier layer comprising an organic solvent has a low specific gravity that to some extent balances the high specific gravity of the surrounded solid particle, reducing the tendency for gravitational settling of the particle. However, the present invention is not limited by this or any other mechanism that can be proposed to explain the surprising findings disclosed herein.

Where disclosure herein relates to an ingredient, in the singular, of any category, including water-soluble active ingredient, water-insoluble active ingredient, organic solvent, emulsifying agent, viscosity modifying agent, etc., it is to be understood that the disclosure embraces a composition comprising a plurality of ingredients of that category, except where the context demands otherwise, such as in description of a specific illustrative example.

The Water-soluble Active Ingredient

In a contemplated composition, most of the volume is occupied by a continuous aqueous phase. This aqueous phase is typically a simple solution of a water-soluble pesticide or plant growth regulator in water, optionally with other ingredients dissolved or dispersed therein as indicated below.

The water-soluble active ingredient can illustratively be a herbicide, plant growth regulator, algicide, fungicide, bactericide, viricide, insecticide, acaricide, nematicide or molluscicide. It can be a water-soluble derivative, such as a salt, of an otherwise water-insoluble pesticide or plant growth regulator. The term "water-soluble" in relation to a pesticide or plant growth regulator or a salt thereof as used herein means having a solubility in deionized water at 20° C. sufficient to enable the water-soluble active ingredient to be dissolved completely in the aqueous phase of a composition of the invention at the desired concentration. Preferred water-soluble active ingredients useful in the present invention have a solubility in deionized water at 20° C. of not less than about 50 g/l, more preferably not less than about 200 g/l. Where an active ingredient compound is referred to herein as being water-soluble, but the compound itself is known not to be water-soluble as defined immediately above, it will be understood that the reference applies to water-soluble derivatives, more particularly water-soluble salts, of the compound.

Water-soluble fungicides and bactericides useful in compositions of the invention illustratively include borax, sec-butylamine, calcium polysulfide, copper sulfate, fosetyl, guazatine, hydroxyquinoline sulfate, iminoctadine, kasugamycin, mercuric chloride, metam, nabam, polyoxin B, propamocarb, validamycin, and/or water-soluble salts thereof. Water-soluble insecticides, acaricides and nematicides useful in compositions of the invention illustratively include acephate, butoxycarboxim, cartap, dicrotophos, formetanate, hydrogen cyanide, methamidophos, methomyl, mevinphos, monocrotophos, nicotine, nitenpyram, omethoate, oxamyl, oxydemeton-methyl, phosphamidon, thiocyclam, trichlorfon, vamidothion, and/or water-soluble salts thereof. Water-soluble plant growth regulators useful in compositions of the invention illustratively include chlormequat, chlorphonium, clofencet, cloxyfonac, cyanamide, daminozide, dikegulac, ethephon, mepiquat, and/or water-soluble salts thereof.

In one embodiment of the invention, the water-soluble active ingredient is a herbicide or an agriculturally acceptable salt thereof. Water-soluble herbicides useful in compositions of the invention include without restriction acifluorfen, acrolein, amitrole, asulam, benazolin, bentazon, bialaphos, bromacil, bromoxynil, chloramben, chloroacetic acid, clopyralid, 2,4-D, 2,4-DB, dalapon, dicamba, dichlorprop, diclofop, difenzoquat, diquat, endothall, fenac, fenoxaprop, flamprop, fluazifop, fluoroglycofen, flupropanate, fomesafen, fosamine, glufosinate, glyphosate, haloxyfop, imazameth, imazamethabenz, imazamox, imazapic, imazapyr, imazaquin, imazethapyr, ioxynil, MCPA, MCPB, mecoprop, methylarsonic acid, naptalam, nonanoic acid, paraquat, picloram, sulfamic acid, 2,3,6-TBA, trichloroacetic acid, triclopyr, and/or water-soluble salts thereof.

Preferred water-soluble herbicides are salts of acid compounds whose molecular structure comprises at least one of each of amine, carboxylate, and either phosphonate or phosphinate functional groups. This category includes salts of the herbicides N-phosphonomethylglycine (glyphosate) and DL-homoalanin-4-yl(methyl)phosphinate (glufosinate). Another preferred group of herbicides are salts of compounds of the imidazolinone class, including imazameth, imazamethabenz, imazamox, imazapic, imazapyr, imazaquin and imazethapyr.

Where the herbicide is cationic or forms cations in the presence of an acid, as for example in the case of difenzoquat, diquat or paraquat, suitable counterions forming an agriculturally acceptable salt illustratively include chloride, bromide, iodide, sulfate, phosphate, acetate and succinate anions.

Where the herbicide is anionic or forms anions in the presence of a base, as for example in the case of most of the herbicides listed above with the exception of difenzoquat, diquat and paraquat, suitable counterions forming an agriculturally acceptable salt illustratively include sodium, potassium, ammonium, organic ammonium and organic sulfonium cations, wherein organic ammonium or organic sulfonium cations have from 1 to about 16 carbon atoms. Preferred organic ammonium cations are dimethylammonium, monoethanolammonium, n-propylammonium and isopropylammonium cations. Preferred organic sulfonium cations are trimethylsulfonium cations.

The water-soluble active ingredient, for example herbicide, is present at a concentration in the composition as a whole sufficient, upon dilution of the composition in a suitable volume of water and applied by spraying to the target locus, to be pesticidally, for example herbicidally, effective. In a concentrate composition it is desirable to provide as high a concentration, or "loading", of the water-soluble active ingredient as is possible and convenient. Depending on the active ingredient in question and the intended use of the composition, a loading of about 50 to about 500 g/l or higher is preferred.

In a particular embodiment, the water-soluble active ingredient is an agriculturally acceptable salt of the herbicide glyphosate. Herbicidal salts of glyphosate were first developed by Monsanto Company and are disclosed, for example, in U.S. Pat. No. 3,799,758, U.S. Pat. No. 3,853, 530, U.S. Pat. No. 4,140,513, U.S. Pat. No. 4,315,765, U.S. Pat. No. 4,405,531, U.S. Pat. No. 4,481,026 and U.S. Pat. No. 4,507,250, the pertinent disclosures of which are incorporated herein by reference.

Although glyphosate has three acid sites, and can therefore form tribasic salts, preferred compositions have an aqueous phase whose pH is not greater than about 8, at which pH value the fraction of glyphosate existing as a tribasic salt is negligibly small. Only the two acid sites that are significantly deprotonated at pH 8 are therefore considered herein. One of these is on the phosphonate moiety, and the other is on the carboxylate moiety, of the glyphosate molecule. Dibasic salts, particularly the diammonium salt, of glyphosate are useful in compositions of the invention, but monobasic salts are generally preferred. Of these, particularly preferred examples include the monosodium, monopotassium, monoammonium, mono (dimethylammonium), mono(ethanolammonium), mono (isopropylammonium) and mono(trimethylsulfonium) salts. Glyphosate a.e. loadings of about 36 to about 480 g/l are achievable; loadings in a range from about 180 to about 360 g a.e./l are found to be especially useful.

The Water-insoluble Active Ingredient

Suspended in the aqueous phase are solid particles of a substantially water-insoluble pesticide or plant growth regulator, sometimes referred to herein for brevity as a "water-insoluble" active ingredient even if it has measurable solubility in water. This active ingredient preferably has a solubility in deionized water at 20° C. not greater than about 100 mg/l. Especially preferred water-insoluble active ingredients useful in the present invention have a solubility in deionized water at 20° C. not greater than about 25 mg/l.

The water-insoluble active ingredient has a melting point not less than about 50° C., preferably not less than about 75° C. Especially preferred water-insoluble active ingredients useful in the present invention have a melting point not less than about 100° C., even more preferably not less than about 150° C.

The water-insoluble active ingredient can illustratively be a herbicide, plant growth regulator, algicide, fungicide, bactericide, viricide, insecticide, acaricide, nematicide or molluscicide.

Water-insoluble fungicides and bactericides useful in compositions of the invention illustratively include azoxystrobin, benalaxyl, benomyl, bitertanol, bromuconazole, captafol, captan, carbendazim, chinomethionat, chlorothalonil, chlozolinate, cyprodinil, dichlofluanid, dichlorophen, diclomezine, dicloran, diethofencarb, dimethomorph, diniconazole, dithianon, epoxiconazole, famoxadone, fenarimol, fenbuconazole, fenfuram, fenpiclonil, fentin, fluazinam, fludioxonil, fluoroimide, fluquinconazole, flusulfamide, flutolanil, folpet, hexachlorobenzene, hexaconazole, imibenconazole, ipconazole, iprodione, kresoxim-methyl, mancozeb, maneb, mepanipyrim, mepronil, metconazole, metiram, nickel bis (dimethyldithiocarbamate), nuarimol, oxine-copper, oxolinic acid, pencycuron, phthalide, procymidone, propineb, quintozene, sulfur, tebuconazole, tecloftalam, tecnazene, thifluzamide, thiophanate-methyl, thiram, tolclofos-methyl, tolylfluanid, triadimefon, triadimenol, triazoxide, triforine, triticonazole, vinclozolin, zineb and ziram.

Water-insoluble insecticides, acaricides and nematicides useful in compositions of the invention illustratively include abamectin, acrinathrin, amitraz, azadirachtin, azamethiphos, azinphos-methyl, azocyclotin, bensultap, bifenthrin, bromopropylate, buprofezin, chlorfenapyr, chlorfenson, chlorfluazuron, clofentezine, coumaphos, cyfluthrin, β-cyfluthrin, cypermethrin, α-cypermethrin, θ-cypermethrin, DDT, deltamethrin, diafenthiuron, dicofol, diflubenzuron, endosulfan, esfenvalerate, etoxazole, fenazaquin, fenbutatin oxide, fenoxycarb, fenpyroximate, fipronil, fluazuron, flucycloxuron, flufenoxuron, halofenozide, γ-HCH, hexaflumuron, hexythiazox, hydramethylnon, lufenuron, methiocarb, methoxychlor, milbemectin, novaluron, pentachlorophenol, pyridaben, resmethrin, rotenone, sulfluramid, tebufenozide, tebufenpyrad, tebupirimfos, teflubenzuron, tetrachlorvinphos, tetradifon, tetramethrin, thiodicarb, tralomethrin, triflumuron and trimethacarb.

Water-insoluble plant growth regulators useful in compositions of the invention illustratively include 6-benzylaminopurine, cyclanilide, flumetralin, forchlorfenuron, inabenfide, 2-(1-naphthyl)acetamide, paclobutrazol, N-phenylphthalamic acid, thidiazuron and uniconazole.

In one embodiment of the invention, the water-insoluble active ingredient is a herbicide. Illustrative examples of such herbicides include aclonifen, atrazine, bensulfuron-methyl, benzofenap, bifenox, bromobutide, bromofenoxim, chlomethoxyfen, chlorbromuron, chlorimuron-ethyl, chlornitrofen, chlorotoluron, chlorthal-dimethyl, clomeprop, daimuron, desmedipham, dichlobenil, diflufenican, dimefuron, dinitramine, diuron, ethametsulfuron-methyl, fenoxaprop-ethyl, flamprop-methyl, flazasulfuron, flumetsulam, flumiclorac-pentyl, flumioxazin, flupoxam, fluridone, flurtamone, isoproturon, isoxaben, isoxapyrifop, lactofen, lenacil, linuron, mefenacet, methabenzthiazuron, metobenzuron, naproanilide, neburon, norflurazon, oryzalin, oxadiazon, oxyfluorfen, phenmedipham, prodiamine, prometryn, propazine, propyzamide, pyrazolynate, pyrazosulfuron-ethyl, pyributicarb, quinclorac, quizalofop-ethyl, rimsulfuron, siduron, simazine, terbuthylazine, terbutryn, thiazopyr, tralkoxydim and trietazine.

In another embodiment of the invention, the water-insoluble active ingredient exhibits chemical degradation in direct contact with an aqueous solution of the selected water-soluble active ingredient. Such chemical degradation can be by hydrolysis or other means and may or may not be pH-sensitive. In this embodiment, the water-insoluble active ingredient is preferably a compound other than one having a —$SO_2NHC(O)NH$— group such as occurs in a sulfonylurea herbicide.

In a particular embodiment of the invention, the water-insoluble active ingredient is a herbicide of the phthalimide class, including those disclosed in U.S. Pat. No. 4,640,707, the pertinent disclosure of which is incorporated herein by reference. Examples of such phthalimide herbicides include 2-[7-fluoro-3,4-dihydro-3-oxo-4-(2-propynyl)-2H-1,4-benzoxazin-6-yl]-4,5,6,7-tetrahydro-1H-isoindole-1,3(2H)-dione (flumioxazin) and [2-chloro-4-fluoro-5-(1,3,4,5,6,7-hexahydro-1,3-dioxo-2H-isoindol-2-yl)phenoxy]acetic acid (flumiclorac) or the pentyl ester thereof (flumiclorac-pentyl). Flumioxazin, having the chemical structure (I)

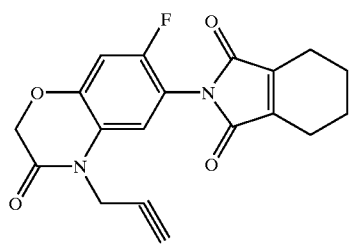

(I)

is preferred. This herbicide was developed by Sumitomo Chemical Company and is available commercially in several countries.

Particle size of the water-insoluble active ingredient is not narrowly critical. The larger the particle size, the more difficult it will be to prevent settling. On the other hand, very small particle sizes increase processing cost as a result of the milling or grinding required and can introduce issues relating to the handling of respirable dusts during manufacturing. Where the water-insoluble active ingredient exhibits chemical degradation, this problem is likely to be exacerbated with excessively small article sizes, because of the correspondingly increased specific surface area. In general, average particle size of about 1–10 μm is found to be satisfactory. In the case of flumioxazin, technical grade powder having an average particle size of about 5 μm is found to provide good suspensions without pre-milling or pre-grinding.

The loading of the water-insoluble active ingredient in the composition as a whole depends on the active ingredient in question and the intended use of the composition. In general this loading is typically about 10 to about 100 g/l.

In a composition of the invention where the water-soluble active ingredient is a salt of the herbicide glyphosate and the water-insoluble active ingredient is the herbicide flumioxazin, the weight ratio of these two herbicides is not narrowly critical, and the precise weight ratio selected can depend on the effect desired. It has been found particularly useful to include these two herbicides in a composition at a weight ratio of glyphosate a. e. to flumioxazin of about 100:1 to about 5:1, more preferably about 30:1 to about 10:1.

The Barrier Layer

In a composition of the invention, a hydrophobic barrier layer surrounds each solid particle of the water-insoluble active ingredient, in intimate contact with the particle and leaving substantially no bare surface of the particle so that substantially no direct contact occurs between the solid particle and the aqueous phase of the composition. The thickness of the barrier layer is not critically important so long as it is effective in isolating the solid particle from the aqueous phase. The barrier layer can take the form of an oil droplet in which are immersed a plurality of solid particles, but it is presently believed that in preferred compositions the predominant form of the barrier layer is a relatively thin hydrophobic shell enclosing a single solid particle. Microscopy techniques familiar to those of skill in the art can be used to determine whether solid particles are predominantly aggregated in individual oil droplets or individually dispersed in the aqueous phase but separated therefrom by a hydrophobic shell.

In one embodiment, the barrier layer comprises a water-immiscible organic solvent. The term "solvent" as used in the present context includes mineral and vegetable oils and derivatives thereof and does not imply a solvency function in compositions of the invention. Indeed, it is preferred that an organic solvent be selected in which the water-insoluble active ingredient is no more than sparingly soluble. For example, the water-insoluble active ingredient preferably has a solubility in the selected organic solvent not greater than about 10 g/l, more preferably not greater than about 1 g/l. However, particularly where the amount of organic solvent present is small relative to the amount of water-insoluble active ingredient present, for example less than about 5 parts by weight of organic solvent per part by weight of water-insoluble active ingredient, rather higher solubility of the water-insoluble active ingredient in the organic solvent, for example up to about 50 g/l, can be acceptable.

Examples of organic solvents which can be suitable in particular cases include without restriction water-immiscible aliphatic and aromatic hydrocarbons and hydrocarbyl alcohols, aldehydes and ketones, mono-, di- and trihydrocarbyl phosphates, silicone and siloxane oils, fatty acids and alkylesters and alkylarnides thereof, and natural vegetable oils whether fractionated or not. Solvents of low volatility are preferred.

A test is provided herein to assist one of skill in the art to select a preferred organic solvent. The procedure for conducting this test is as follows.

1. Water and a candidate organic solvent are mixed with agitation in a glass vessel in approximately equal volumes. Optionally, the selected water-soluble active ingredient can first be dissolved in the water at a concentration similar to that desired in the composition to be developed.

2. The mixture thus formed is allowed to stand for a period of a few minutes to one hour without agitation. If the mixture exhibits no phase separation, the candidate organic solvent is deemed to be miscible in water and is rejected. If the mixture separates into an upper oil phase and a lower water phase, the candidate organic solvent is deemed to be water-immiscible and proceeds to the next stage of the test.

3. The mixture is agitated again, and a suitable amount (no more than about 1% by weight of the contents of the glass vessel) of the selected water-insoluble active ingredient in particulate form is added to the mixture. Agitation is continued for a few minutes to homogenize the mixture.

4. The resulting mixture is allowed to stand without agitation, until the upper and lower phases have clearly separated again. The contents of the glass vessel are carefully examined to determine which one of the three following outcomes 5, 6 or 7 applies.

5. If no particles of the water-insoluble active ingredient are visible, it is presumed that the added particles have dissolved in the organic solvent. In such a case the candidate organic solvent is not preferred, and will normally be rejected.

6. If at least some particles of the water-insoluble active ingredient are visible in the lower (water) phase, the candidate organic solvent is not preferred, and is normally rejected, even if a large majority of the particles remain in the upper (oil) phase. Note that particularly careful observation is required at this stage. The candidate organic solvent is acceptable if particles visible in the lower phase are clearly contained within oil droplets, but is normally not acceptable if the particles appear to be directly immersed in water. In case of doubt, it can be useful to repeat the procedure from step 3 and determine the outcome a second time.

7. If substantially all visible particles of the water-insoluble active ingredient are found in the upper (oil) phase or in oil droplets in the lower (water) phase, it is confirmed that the particles have much greater affinity for the organic solvent than for water, and the candidate organic solvent is deemed suitable for use in a composition of the invention.

Especially preferred organic solvents, when subjected to the above test, form a discrete upper phase with no droplets remaining in the lower phase, so that all particles of the water-insoluble active ingredient migrate above the phase boundary even if the particles have a specific gravity significantly greater than 1.

Illustratively, where the water-insoluble active ingredient is the herbicide flumioxazin, a useful organic solvent for the barrier layer, identified by the above test, is phenylxylylethane, available for example as Sorpol™ 7065 from Toho Chemical Corp. Another useful organic solvent is an alkylaryl phosphate, available for example as Santicizer™ 141 from Solutia Inc.; 2-ethylhexyl diphenyl phosphate is particularly useful.

Where the water-insoluble ingredient is chemically degradable in the presence of water, it is especially advantageous to select for the barrier layer an organic solvent in which the water-insoluble ingredient is of very low solubility. For example, where the water-insoluble active ingredient is flumioxazin, it is strongly preferred not to use as the barrier layer a solvent such as benzyl acetate in which flumioxazin is rather soluble. It has been found that chemical degradation of flumioxazin is much more rapid when benzyl acetate is the organic solvent, than when a solvent such as phenylxylylethane, in which flumioxazin is only very sparingly soluble, is used. It is believed, without being bound by theory, that the advantage in this situation of phenylxylylethane over benzyl acetate results from the greatly reduced exposure of flumioxazin molecules to the aqueous phase when the flumioxazin remains in solid particulate form surrounded by a barrier layer.

The organic solvent forming the barrier layer in this embodiment of the invention forms a discontinuous oil phase dispersed in the aqueous phase. To stabilize this dispersion, one or more emulsifying agents are normally required. Suitable emulsifying agents can be selected by routine experimentation once a suitable organic solvent has been identified. However, it is important that at least one of the emulsifying agent(s) selected be lipophilic or of low water solubility, which in the present context means having an HLB not greater than about 15, preferably not greater than about 13, and more preferably not greater than about 11. Anionic and nonionic emulsifying agents of HLB not greater than about 11 are especially preferred.

As illustration, in compositions of the invention using glyphosate isopropylammonium salt as the water-soluble active ingredient, flumioxazin as the water-insoluble active ingredient and phenylxylylethane as the organic solvent, a suitable emulsifying system comprises a cationic emulsifying agent selected from $C_{12-18}$ alkylammonium salts, $C_{12-18}$ alkyltrimethylammonium salts, di($C_{12-18}$ alkyl) dimethylammonium salts, polyoxyalkylene $C_{12-18}$ alkylammonium salts, benzalkonium chloride, etc., and an anionic emulsifying agent selected from polyoxyalkylene $C_{12-18}$ alkylether sulfates and phosphates, polyoxyalkylene $C_{12-18}$ alkyl sulfates, polyoxyalkylene $C_{12-18}$ alkylphenyl sulfates, sulfonates and phosphates, etc. One of these emulsifying agents, typically the cationic one, can be relatively hydrophilic or water-soluble, but it is important that the other, typically the anionic emulsifying agent, be lipophilic or of low water solubility. An example of such an emulsifying system consists of Sorpol™ 7830P of Toho Chemical Corp. (an anionic polyoxyethylene alkylether phosphate having HLB=10.5) and Sorpol™ 7377P of Toho Chemical Corp. (a water-soluble cationic polyoxyethylene alkylammonium salt, HLB value not available) in a weight ratio of about 1:1 to about 1:5. Another example consists of the same two emulsifying agents together with New Kalgen™ 4016EHB of Takemoto (a nonionic polyoxyethylene/ polyoxypropylene block opolymer having HLB=8.0) in an amount approximately equal to that of the anionic emulsifying agent.

In another embodiment of the invention, the barrier layer contains no organic solvent, and consists essentially of an emulsifying system comprising one or more emulsifying agents having an HLB not greater than about 15, preferably not greater than about 13, and more preferably not greater than about 11. The emulsifying agents useful in this embodiment are illustratively those exemplified above.

As further guidance in selecting suitable emulsifying agents, with or without an organic solvent, and suitable amounts of these ingredients, to form a barrier layer, it has been found that a good test is to prepare a composition containing all desired ingredients with the exception of the solid particulate water-insoluble active ingredient. This composition normally takes the form of an emulsion. If the emulsion is turbid or milky, indicating that micelles or oil phase particles are larger than about 1 μm, this is generally an indication that a suitable barrier layer can be produced. If, on the other hand, the emulsion is clear, the selected ingredients are likely to be less useful in creating a suitable barrier layer.

Viscosity Modifying Agent

According to the present invention, by intimately surrounding the suspended solid particles with a barrier layer, enhanced resistance to settling or sedimentation of the solid particles is unexpectedly achieved. However, in some embodiments it is desirable to further enhance resistance to settling or sedimentation by including in the aqueous phase of the composition a viscosity modifying agent.

Any viscosity modifying agent known in the art can be used. However, if a polymer thickener such as xanthan gum is used, not only is viscosity increased but a significant increase in elasticity is also observed. This tends to produce "stringiness" in the composition, which can interfere with the process of packaging the composition and can reduce dispersibility when the composition is diluted in water by the end-user.

The preferred method of increasing viscosity in compositions of the present invention exploits the tendency of small particles, when dispersed in an aqueous suspension, to form linear chains in the absence of agitation, and the tendency of such chains to form three-dimensional network-like structures throughout the composition. These tendencies increase as the particles become smaller. The resulting structural viscosity inhibits settling of particles.

Thus, miniaturization of the particles would be an effective way to inhibit settling. However, pulverization of the water-insoluble pesticide into small enough particles to impart sufficient structural viscosity adds significant cost and may not be practicable. Moreover, the desired concentration of the water-insoluble pesticide is often too low to provide sufficient structural viscosity, even if milled to ultrafine dimensions.

A more preferred method of inhibiting settling is therefore to add a biologically inert nanoparticulate material to increase structural viscosity. If that material is hydrophilic, the concentration required to impart the desired structural viscosity can be very low. A particularly useful material for this purpose is colloidal hydrophilic silica, commercially available, for example, from Degussa under the trademark Aerosil™. Typical concentrations of colloidal hydrophilic silica in compositions of the invention are about 0.1% to about 5% by weight, for example about 0.5% to about 2% by weight. A wide range of nanoparticle sizes can be used, with a presently preferred range being about 10 to about 40 nm.

Where the water-soluble active ingredient is a salt of the herbicide glyphosate, it was initially feared that addition of colloidal hydrophilic silica might reduce herbicidal effectiveness by adsorption of glyphosate to the silica. A test was therefore conducted to determine the degree of adsorption of glyphosate by the highest concentration of colloidal hydrophilic silica likely to be used in a composition of the invention, i.e. 5% by weight, and by even higher concentrations.

The procedure for this test is to add a weighed amount of Aerosil™ COK-84 colloidal hydrophilic silica to a measured volume of glyphosate isopropylammonium salt solution of known concentration (23% a.e. by weight) in a stoppered glass bottle and agitate gently at a temperature of 20° C. for 16 hours. The solution is then centrifuged to deposit the silica, leaving a clear supernatant. The supernatant is analyzed for glyphosate by HPLC. The amount of adsorption is calculated from the reduction in glyphosate concentration in the supernatant solution by comparison with the initial concentration.

Results of this test are presented in Table 2. At a silica concentration of 5%, the degree of adsorption of glyphosate was negligible. Thus colloidal hydrophilic silica at 5% or less in a composition of the invention is not expected to have any negative impact on herbicidal effectiveness.

TABLE 2

Adsorption of glyphosate from a 23% a.e. aqueous solution of glyphosate isopropylammonium salt by colloidal hydrophilic silica

| silica concentration (%) | glyphosate adsorption (%) |
|---|---|
| 0 | 0 |
| 5 | 2 |
| 10 | 12 |
| 20 | 40 |

A herbicidal effectiveness test on "inutade" and "tsuyukusa" (Table 3) demonstrates that addition of colloidal hydrophilic silica at the high rate of 300 g/ha (equivalent to a concentration of 6% by weight in a concentrate composition containing 24% glyphosate a.e.) does not reduce herbicidal effectiveness of a glyphosate-flumioxazin composition of the invention. Indeed, silica appeared to provide some further enhancement of herbicidal effectiveness, particularly on "tsuyukusa". Similar enhancing effects of colloidal hydrophilic silica have been reported in co-assigned International Pat. Publication No. WO 98/17108.

TABLE 3

Herbicidal effectiveness with and without colloidal hydrophilic silica

| | | | percent inhibition weed species: | | | | | | |
|---|---|---|---|---|---|---|---|---|---|
| | | | inutade | | | | tsuyukusa | | |
| glyphosate | flumioxazin | silica | DAT: | | | | | | |
| g a.e./ha | g/ha | g/ha | 3 | 7 | 20 | 27 | 3 | 7 | 20 | 27 |
| 1200 | 60 | 0 | 1 | 30 | 90 | 96 | 16 | 72 | 96 | 99 |
| 1200 | 60 | 300 | 1 | 33 | 93 | 97 | 31 | 85 | 99 | 100 |

Although colloidal hydrophilic silica can enhance resistance to settling of solid particulates such as those used in compositions of the present invention, a potential problem is settling of the silica particles themselves. It has surprisingly been found that compositions of the invention generally exhibit reduced settling not only of solid particles of a water-insoluble active ingredient by comparison with otherwise similar compositions lacking a barrier layer, but also of silica particles added as a viscosity modifying agent.

Other Optional Ingredients

Compositions of the invention can optionally contain inert or excipient ingredients other than those mentioned above, provided such ingredients do not destabilize the composition, either chemically or physically. Examples of such ingredients include dyes, foam moderating agents, drift control agents, pour point depressants (for example propylene glycol or polypropylene glycol) and surfactants other than those used as emulsifying agents.

The pH of the Aqueous Phase

Even in the presence of a barrier layer as provided by the present invention, some small amount of migration of the water-insoluble active ingredient can occur through the barrier layer. If the water-insoluble active ingredient is susceptible to degradation in the presence of water, some small degree of degradation can therefore occur. Such degradation, for example hydrolytic degradation, is in many cases pH-sensitive. Thus it is preferred in the present invention to control the pH of the aqueous phase to a range wherein such degradation is minimized.

It has been found, for example, that in a composition of the invention wherein the aqueous phase comprises a solution of mono(isopropylammonium) glyphosate having a pH of about 4.5 to about 5, chemical degradation of flumioxazin is insignificant, even at elevated temperatures. However, if pH of the aqueous phase is raised, for example by addition of a base or by use of a dibasic salt of glyphosate, a significant increase in the rate of degradation is evident.

Where the water-insoluble active ingredient is flumioxazin, it is therefore preferred that pH of the aqueous phase be not greater than about 6, more preferably not greater than about 5.5. Where the water-soluble active ingredient is a salt that results in a pH greater than about 6, it is preferred to lower the pH of the aqueous phase to less than about 6, more preferably less than about 5.5, by addition of an acid.

Process of Preparing a Composition of the Invention

A process that has been found suitable for preparing a composition of the invention is described below. However, compositions of the invention are not limited to compositions made by this process.

First, in a suitable vessel, a measured amount of a particulate solid water-insoluble pesticidal or plant growth regulating active ingredient is added to a measured amount of an organic solvent selected as described above. A measured amount of each desired emulsifying agent is also added. These ingredients are mixed thoroughly to provide a homogeneous suspension of the water-insoluble active ingredient in the organic solvent. Optionally the organic solvent can be omitted, in which case the water-insoluble active ingredient is suspended in the emulsifying agent(s).

An aqueous premix is prepared in another vessel by dissolving a measured amount of a water-soluble pesticidal or plant growth regulating active ingredient in a measured amount of water. If the water-soluble active ingredient is supplied as an aqueous solution, this solution can itself form the aqueous premix or it can be diluted with water as necessary to form the aqueous premix. A foam moderating agent and/or other optional excipient ingredients, but not at this stage a viscosity moderating agent, can be added to the aqueous premix.

To the suspension of the water-insoluble active ingredient, under agitation, is slowly added a first measured portion of the aqueous premix. Optionally, a measured amount of a viscosity moderating agent such as colloidal hydrophilic silica is now added and the mixture is agitated, for example by stirring, until it is homogeneous. Typically at this point the mixture has high viscosity and, if colloidal hydrophilic silica has been added, a creamy consistency. The remaining portion of the aqueous premix is now added, under continuing agitation, during which the viscosity decreases rapidly, to produce a finished composition of the invention.

Method of Use of a Composition of the Invention

Pesticides and plant growth regulators are applied to a locus such as soil or the foliage of plants at a rate sufficient to give the desired pesticidal or plant growth regulating effect. This application rate is usually expressed as amount of pesticidal or plant growth regulating active ingredient per unit area treated, e.g. grams per hectare (g/ha). What constitutes a "desired effect" varies according to the standards and practice of those who investigate, develop, market and use a specific class of pesticides or plant growth regulators. For example, in the case of a herbicide, the amount applied per unit area to give 85% control of a plant species as measured by growth reduction or mortality is often used to define a commercially effective rate.

The selection of application rates that are biologically effective for a specific pesticide and/or plant growth regulator package-mix composition is within the skill of the ordinary agricultural scientist. Those of skill in the art will likewise recognize that individual plant conditions, weather and growing conditions, as well as the specific active ingredients and their weight ratio in the composition, will influence the degree of biological effectiveness achieved in practicing this invention. With respect to the use of a composition of the invention containing glyphosate herbicide, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

Herbicidal compositions of glyphosate salts are used to control a very wide variety of plants worldwide. Package-mix compositions of the present invention containing a glyphosate salt and a solid water-insoluble herbicide such as flumioxazin can likewise effectively control a wide range of plants, in some cases more effectively than glyphosate salt alone.

Particularly important annual dicotyledonous plant species for control of which a glyphosate-containing composition of the invention can be used are exemplified without limitation by velvetleaf (*Abutilon theophrasti*), pigweed (Amaranthus spp.), buttonweed (Borreria spp.), oilseed rape, canola, indian mustard, etc. (Brassica spp.), commelina (Commelina spp.), filaree (Erodium spp.), sunflower (Helianthus spp.), momingglory (Ipomoea spp.), kochia (*Kochia scoparia*), mallow (Malva spp.), wild buckwheat, smartweed, etc. (Polygonum spp.), purslane (Portulaca spp.), russian thistle (Salsola spp.), sida (Sida spp.), wild mustard (*Sinapis arvensis*) and cocklebur (Xanthium spp.).

Particularly important annual monocotyledonous plant species for control of which a glyphosate-containing composition of the invention can be used are exemplified without limitation by wild oat (*Avena fatua*), carpetgrass (Axonopus spp.), downy brome (*Bromus tectorum*), crabgrass (Digitaria spp.), barnyardgrass (*Echinochloa crusgalli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (Phalaris spp.), foxtail (Setaria spp.), wheat (*Triticum aestivum*) and corn (*Zea mays*).

Particularly important perennial dicotyledonous plant species for control of which a glyphosate-containing composition of the invention can be used are exemplified without limitation by mugwort (Artemisia spp.), milkweed (Asclepias spp.), canada thistle (*Cirsium arvense*), field bindweed (*Convolvulus arvensis*) and kudzu (Pueraria spp.).

Particularly important perennial monocotyledonous plant species for control of which a glyphosate-containing composition of the invention can be used are exemplified without limitation by brachiaria (Brachiaria spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (Phragmites spp.), johnsongrass (*Sorghum halepense*) and cattail (Typha spp.).

Other particularly important perennial plant species for control of which a glyphosate-containing composition of the invention can be used are exemplified without limitation by horsetail (Equisetum spp.), bracken (*Pteridium aquilinum*), blackberry (Rubus spp.) and gorse (*Ulex europaeus*).

In a particular contemplated method of use of a glyphosate-containing composition of the invention, the composition, following dilution in water, is applied to foliage of crop plants genetically transformed or selected to tolerate glyphosate, and simultaneously to foliage of weeds or undesired plants growing in close proximity to such crop plants. In this case it is important that the water-insoluble active ingredient also present in the composition, for example the herbicide flumioxazin, is not phytotoxic to the crop species at the rate used. This method of use results in control of the weeds or undesired plants while leaving the crop plants substantially unharmed. Crop plants genetically transformed or selected to tolerate glyphosate include those whose seeds are sold by Monsanto Company or under license from Monsanto Company bearing the Roundup Ready® trademark. These include varieties of cotton, soybean, canola and corn. Glyphosate-flumioxazin compositions of the invention are particularly useful for selective weed control in glyphosate-tolerant soybeans.

Plant treatment compositions can be prepared simply by diluting a concentrate composition of the invention in water. Application of plant treatment compositions to a locus is preferably accomplished by spraying, using any conventional means for spraying liquids, such as spray nozzles, atomizers or the like. Compositions of the invention can be used in precision farming techniques, in which apparatus is employed to vary the amount of pesticide applied to different parts of a field, depending on variables such as the particular plant species present, soil composition, etc. In one embodiment of such techniques, a global positioning system operated with the spraying apparatus can be used to apply the desired amount of the composition to different parts of a field.

A plant treatment composition is preferably dilute enough to be readily sprayed using standard agricultural spray equipment. Useful spray volumes for the present invention can range from about 25 to about 1000 liters per hectare (l/ha) or higher, preferably about 100 to about 500 l/ha, by spray application.

EXAMPLES

The following Examples are provided for illustrative purposes only and are not intended to limit the scope of the present invention. The Examples will permit better understanding of the invention and perception of its advantages and certain variations of execution.

Example 1

A composition of the invention containing glyphosate isopropylammonium salt and flumioxazin as detailed in Table 4 is prepared by a procedure described below.

TABLE 4

Composition of Example 1 (total 1000 g)

| Component | g |
|---|---|
| flumioxazin suspension premix | |
| flumioxazin (99.4%) | 12.5 |
| Phenylxylylethane, Sorpol ™ 7065 | 25.0 |
| emulsifying agent, Sorpol ™ 7830P | 31.0 |
| emulsifying agent, Sorpol ™ 7377P | 41.0 |
| propylene glycol | 21.0 |
| Total | 130.5 |
| glyphosate aqueous premix | |
| glyphosate isopropylammonium salt (62% aqueous) | 500.0* |
| deionized water | 353.5 |
| silicone antifoam, Shin-etsu ™ KM-90 (10%) | 1.0 |
| Total | 854.5 |
| viscosity modifying agent | |
| Colloidal hydrophilic silica, Aerosil ™ COK-84 | 15.0 |

*equivalent to 310.0 g glyphosate isopropylammonium salt; 230.0 g glyphosate a.e.

In a 1.5 liter formulation tank, 12.5 g flumioxazin powder, 25 g Sorpol™ 7065, 31 g Sorpol™ 7830P, 41 g Sorpol™ 7377P and 21 g propylene glycol are mixed thoroughly until homogeneous, to form a flumioxazin suspension premix.

In a 1 liter formulation tank, 500 g of a 62% aqueous solution of glyphosate isopropylamnnonium salt, 1 g Shinetsu™ KM-90 and 353.5 g deionized water are mixed to form a glyphosate aqueous premix.

While agitating the flumioxazin suspension premix, 140 g of the glyphosate aqueous premix is slowly added, to provide a water-in-oil emulsion containing solid particles of flumioxazin suspended in the oil phase. Next, 15 g Aerosil™ COK-84 is added with continuing agitation to give a mixture with high viscosity and a creamy consistency. Finally, the remaining 714.5 g of the glyphosate aqueous premix is slowly added with continuing agitation, during which viscosity decreases rapidly, to produce a finished composition of the invention.

Example 2

A composition of the invention containing glyphosate isopropylammonium salt and flumioxazin as detailed in Table 5 is prepared by a procedure similar to that for Example 1, but using Santicizer™ 141 as the organic solvent.

TABLE 5

Composition of Example 2 (total 1000 g)

| Component | g |
|---|---|
| flumioxazin suspension premix | |
| flumioxazin (99.4%) | 12 |
| organic solvent, Santicizer ™ 141 | 20 |
| emulsifying agent, Sorpol ™ 7830P | 31 |
| emulsifying agent, Sorpol ™ 7377P | 41 |
| propylene glycol | 28 |
| total | 132 |

TABLE 5-continued

Composition of Example 2 (total 1000 g)

| Component | g |
|---|---|
| glyphosate aqueous premix | |
| glyphosate isopropylammonium salt (62% aqueous) | 500* |
| deionized water | 352 |
| silicone antifoam, Shin-etsu ™ KM-90 (10%) | 1 |
| Total | 853 |
| viscosity modifying agent | |
| colloidal hydrophilic silica, Aerosil ™ COK-84 | 15 |

*equivalent to 310 g glyphosate isopropylammonium salt; 230 g glyphosate a.e.

Example 3

A composition of the invention containing glyphosate isopropylammonium salt and flumioxazin as detailed in Table 6 is prepared by a procedure similar to that for Example 1, but using Vinicizer™ 40 of Kao Corporation as the organic solvent. An additional emulsifying agent, New Kalgen™ 4016EHB, is used.

TABLE 6

Composition of Example 3 (total 1000 g)

| Component | g |
|---|---|
| flumioxazin suspension premix | |
| flumioxazin (99.4%) | 12 |
| organic solvent, Vinicizer ™ 40 | 15 |
| emulsifying agent, Sorpol ™ 7830P | 47 |
| emulsifying agent, Sorpol ™ 7377P | 62 |
| emulsifying agent, New Kalgen ™ 4016EHB | 50 |
| propylene glycol | 10 |
| total | 196 |
| glyphosate aqueous premix | |
| glyphosate isopropylammonium salt (62% aqueous) | 500* |
| deionized water | 288 |
| silicone antifoam, Shin-etsu ™ KM-90 (10%) | 1 |
| total | 789 |
| viscosity modifying agent | |
| colloidal hydrophilic silica, Aerosil ™ COK-84 | 15 |

*equivalent to 310 g glyphosate isopropylammonium salt; 230 g glyphosate a.e.

Example 4

A composition of the invention containing glufosinate ammonium salt and flumioxazin as shown in Table 7 is prepared by a procedure similar to that for Example 1.

TABLE 7

Composition of Example 4 (total 1000 g)

| Component | g |
|---|---|
| flumioxazin suspension premix | |
| flumioxazin (99.4%) | 12 |
| phenylxylylethane, Sorpol ™ 7065 | 20 |
| emulsifying agent, Sorpol ™ 7830P | 31 |

TABLE 7-continued

Composition of Example 4 (total 1000 g)

| Component | g |
|---|---|
| emulsifying agent, Sorpol ™ 7377P | 41 |
| propylene glycol | 28 |
| total | 132 |
| glufosinate aqueous premix | |
| glufosinate ammonium salt (50% aqueous) | 500* |
| deionized water | 352 |
| silicone antifoam, Shin-etsu ™ KM-90 (10%) | 1 |
| total | 853 |
| viscosity modifying agent | |
| colloidal hydrophilic silica, Aerosil ™ COK-84 | 15 |

*equivalent to 250 g glufosinate ammonium salt

Example 5

A composition of the invention containing dicamba isopropylammoniumn salt and flumioxazin as detailed in Table 8 is prepared. The procedure is similar to that for Example 1.

TABLE 8

Composition of Example 5 (total 1000 g)

| Component | g |
|---|---|
| flumioxazin suspension premix | |
| flumioxazin (99.4%) | 12 |
| phenylxylylethane, Sorpol ™ 7065 | 20 |
| emulsifying agent, Sorpol ™ 7830P | 31 |
| emulsifying agent, Sorpol ™ 7377P | 41 |
| propylene glycol | 28 |
| total | 132 |
| dicamba aqueous premix | |
| dicamba isopropylammonium salt (40% a.e., aqueous) | 500* |
| deionized water | 352 |
| silicone antifoam, Shin-etsu ™ KM-90 (10%) | 1 |
| total | 853 |
| viscosity modifying agent | |
| colloidal hydrophilic silica, Aerosil ™ COK-84 | 15 |

*equivalent to 200 g dicamba a.e.

Example 6

A composition of the invention containing MCPA isopropylammonium salt and flumioxazin as detailed in Table 9 is prepared. The procedure is similar to that for Example 1.

TABLE 9

Composition of Example 6 (total 1000 g)

| Component | g |
|---|---|
| flumioxazin suspension premix | |
| flumioxazin (99.4%) | 12 |
| phenylxylylethane, Sorpol ™ 7065 | 20 |
| emulsifying agent, Sorpol ™ 7830P | 31 |

TABLE 9-continued

Composition of Example 6 (total 1000 g)

| Component | g |
| --- | --- |
| emulsifying agent, Sorpol ™ 7377P | 41 |
| propylene glycol | 28 |
| total | 132 |
| MCPA aqueous premix | |
| MCPA isopropylammonium salt (30% a.e., aqueous) | 500* |
| deionized water | 352 |
| silicone antifoam, Shin-etsu ™ KM-90 (10%) | 1 |
| total | 853 |
| viscosity modifying agent | |
| colloidal hydrophilic silica, Aerosil ™ COK-84 | 15 |

*equivalent to 150 g MCPA a.e.

Example 7

Eight compositions A-H were made by a process similar to that used in Example 1, in order to determine the effect of the barrier layer of the invention on chemical stability of flumioxazin as measured by HPLC, following storage at 60° C. for 50 days. This is a very extreme storage stability test, believed to be equivalent to storage under normal conditions over a period of 3–4 years.

As a comparative standard, a simple dispersion of flumioxazin particles, at a concentration of 2.2% by weight, in a 31% aqueous solution of glyphosate isopropylammonium salt was subjected to the same test. It was found that significant chemical degradation of flumioxazin had occurred in this comparative standard under these extreme conditions.

A series of eight compositions A'–H', similar to compositions A–H respectively except that no flumioxazin was included, to determine if the composition in the absence of suspended solid particles of flumioxazin was clear or milky.

Details of compositions A–H, and observations relating to appearance of compositions A'–H' without flumioxazin as well as observations on chemical degradation of flumioxazin, are presented in Table 10.

TABLE 10

Effect of a barrier layer as defined herein on chemical degradation of flumioxazin in compositions stored for 50 days at 60° C.

| | A | B | C | D | E | F | G | H |
| --- | --- | --- | --- | --- | --- | --- | --- | --- |
| glyphosate isopropylammonium salt, % | 31.0 | 31.0 | 31.0 | 31.0 | 31.0 | 31.0 | 31.0 | 31.0 |
| flumioxazin, % | 2.2 | 2.2 | 2.2 | 2.2 | 2.2 | 2.2 | 2.2 | 2.2 |
| organic solvent | | | | | | | | |
| Sorpol ™ 7065, % | 2.5 | 2.5 | 2.5 | — | — | — | — | — |
| Santicizer ™ 141, % | — | — | — | 2.5 | — | — | — | — |
| Vinicizer ™ 40, % | — | — | — | — | 2.5 | — | — | — |
| emulsifying agent | | | | | | | | |
| Sorpol ™ 7830[1], % | 3.0 | 3.0 | — | 3.0 | 3.0 | — | — | — |
| Sorpol ™ 7377[2], % | 4.5 | — | — | 4.5 | 4.5 | — | 4.5 | — |
| Sorpol ™ T-10[3], % | — | — | — | — | — | 3.0 | — | — |
| sucrose fatty acid ester[4], % | — | — | — | — | — | — | — | 4.5 |
| water, % | 56.8 | 61.3 | 64.3 | 56.8 | 56.8 | 63.8 | 62.3 | 62.3 |
| appearance without solid flumioxazin particles[5] | M | M | M | M | M | M | C | C |
| barrier layer? | yes | yes | yes | yes | yes | yes | no | no |
| degradation of flumioxazin significantly reduced? | yes | yes | yes | yes | yes | yes | no | no |

[1]anionic emulsifying agent of Toho Chemical Corp., HLB = 10.5
[2]water-soluble cationic emulsifying agent of Toho Chemical Corp., HLB not available
[3]nonionic emulsifying agent of Toho Chemical Corp., HLB = 10
[4]nonionic emulsifying agent of Toho Chemical Corp., HLB = 16
[5]appearance of compositions A'–H' as described in the text; M = milky; C = clear In the absence of flumioxazin, compositions A'–F' containing an organic solvent and/or a lipophilic emulsifying agent all formed milky emulsions. Compositions A–F all form a barrier layer intimately surrounding each solid particle of flumioxazin, and all were found in this study to exhibit significantly reduced chemical degradation of flumioxazin by comparison with that seen in a simple dispersion of flumioxazin in aqueous glyphosate salt solution. In none of compositions A–F, under the severe conditions of this test, did chemical degradation of flumioxazin exceed 10%.

By contrast, compositions G' and H' containing no organic solvent and only a hydrophilic emulsifying agent were clear in appearance, in the absence of flumioxazin. They contained no ingredient capable of forming a barrier layer as required in the present invention. Chemical degradation of flumioxazin in compositions G and H was not reduced by comparison with that seen in the comparative standard (a simple dispersion of flumioxazin in aqueous glyphosate salt solution).

Thus, the compositions of this Example clearly illustrate the importance of the carrier layer as herein disclosed for protecting flumioxazin from chemical degradation that would occur if the flumioxazin were in direct contact with the aqueous glyphosate salt solution.

Example 8

The compositions of Examples 1–6 were stored at room temperature for 6 months, after which time they were examined for settling of the solid particulate. No settling was seen in any of the six compositions.

The same compositions were stored at 60° C. for 1 month, after which time chemical degradation of flumioxazin was determined by HPLC. Parallel compositions, similar to those of the invention exemplified in Examples 1–6 but in each case lacking a barrier layer (i.e., having no organic solvent or lipophilic emulsifying agent, only the hydrophilic emulsifying agent Sorpol™ 7377P) were subjected to the same storage conditions and chemical degradation analysis. The amount of chemical degradation seen in the compositions of the invention was expressed as a fraction of that seen in the parallel compositions lacking a barrier layer. Results are presented in Table 11.

TABLE 11

Relative chemical degradation of flumioxazin in compositions with and without a barrier layer, when stored at 60° C. for 1 month

| Example | Degradation with barrier layer, as fraction of degradation without barrier layer |
| --- | --- |
| 1 | 0.024 |
| 2 | 0.089 |
| 3 | 0.045 |
| 4 | 0.050 |
| 5 | 0.075 |
| 6 | 0.089 |

All six compositions of Examples 1–6 thus exhibited excellent resistance to chemical degradation of flumioxazin by comparison with otherwise similar compositions lacking a barrier layer.

Example 9

A composition of the invention containing glyphosate isopropylammonium salt and flumioxazin as detailed in Table 12 is prepared by the procedure of Example 1.

TABLE 12

Composition of Example 9 (total 1000 g)

| Component | g |
| --- | --- |
| flumioxazin suspension premix | |
| flumioxazin (99.4%) | 11 |
| phenylxylylethane, Sorpol ™ 7065 | 25 |
| emulsifying agent, Sorpol ™ 7830P | 31 |
| emulsifying agent, Sorpol ™ 7377P | 41 |
| propylene glycol | 21 |
| total | 129 |
| glyphosate aqueous premix | |
| glyphosate isopropylammonium salt (62% aqueous) | 476* |
| deionized water | 379 |
| silicone antifoam, Shin-etsu ™ KM-90 (10%) | 1 |
| total | 856 |
| viscosity modifying agent | |
| colloidal hydrophilic silica, Aerosil ™ COK-84 | 15 |

*equivalent to 300 g glyphosate isopropylammonium salt; 220 g glyphosate a.e.

In addition to this composition of the invention, otherwise similar compositions were prepared with the omission of either (a) the phenylxylylethane organic solvent or (b) the colloidal hydrophilic silica (these ingredients were replaced by water). A rapid test was conducted to assess differences in physical stability, in which each of these compositions was diluted 50 times with water and settling behavior noted after 10 hours and again after 3 days.

Not unexpectedly, the composition lacking a viscosity modifying agent (silica) exhibited significant settling in 10 hours and almost complete settling in 3 days of the solid particulate flumioxazin, leaving a clear supernatant. The composition having a viscosity modifying agent (silica) but lacking an organic solvent in a barrier layer exhibited significant settling in 10 hours to 3 days, leaving a partially cleared supernatant. Most unexpectedly at such dilution, the diluted composition of Table 12 including both organic solvent and silica exhibited no settling. The diluted composition, even after 3 days, remained uniformly turbid from top to bottom.

This remarkable result indicates a further unexpected advantage of compositions of the invention, namely that if diluted in a spray tank and left for a period of several hours, for example overnight, to several days without agitation, problems of sedimentation are much reduced by comparison with those experienced with typical suspension compositions, even those containing an effective viscosity modifying agent such as colloidal hydrophilic silica. It is common for agricultural spray operators to prepare a diluted spray composition, intending to apply it immediately, but to be interrupted by rain or another adverse situation, which may last for hours or days. Typically, with suspension compositions known in the art, the spray tank has to be kept agitated until spraying can be resumed, otherwise the solid particulate component of the suspension settles and can form a deposit on the bottom of the tank that is difficult or impossible to resuspend. A new solution to this problem is therefore provided herein.

The result seen in Example 9 also serves as a likely indicator of enhanced long-term physical stability of the undiluted concentrate composition of Table 12 by comparison with an otherwise similar composition lacking only the organic solvent of the barrier layer.

Example 10

The composition of the invention described in Example 9 (Table 12) was subjected to another physical stability test, alongside otherwise similar compositions prepared with the omission of either (a) the phenylxylylethane organic solvent or (b) the colloidal hydrophilic silica as described in Example 9. In this test, each of these compositions was diluted 5 times with water and settling behavior was noted after 3 days. This test, more than the test of Example 9, can be considered as an indicator of long-term physical stability of undiluted concentrate compositions.

Not unexpectedly, the composition lacking a viscosity modifying agent (silica) again exhibited almost complete settling in 3 days of the solid particulate flumioxazin, leaving a clear supernatant. The composition having a viscosity modifying agent (silica) but lacking an organic solvent in a barrier layer again exhibited significant settling in 3 days, leaving a partially cleared supernatant. As was observed with the more dilute test composition of Example 9, the composition of Table 12 including both organic solvent and silica, diluted 5 times with water, exhibited no settling. The diluted composition, even after 3 days, remained uniformly turbid from top to bottom.

The results of this test, when considered together with the results of the test of Example 9, demonstrate that the enhanced physical stability provided by compositions of the invention, by comparison with those relying for physical stability on colloidal hydrophilic silica alone, is not peculiar to highly diluted systems. The excellent long-term physical stability observed with concentrate compositions of the invention illustrated herein is therefore at least in part due to the novel barrier layer provided by the present invention.

Example 11

A composition of the invention containing glyphosate ammonium salt and flumioxazin.as detailed in Table 13 is prepared. The procedure is similar to that for Example 1.

TABLE 3

Composition of Example 11 (total 1000 g)

| component | g |
| --- | --- |
| flumioxazin suspension premix | |
| flumioxazin (99.4%) | 12.5 |
| phenylxylylethane, Sorpol ™ 7065 | 25.0 |
| emulsifying agent, Sorpol ™ 7830P | 32.0 |
| emulsifying agent, Sorpol ™ 7377P | 54.0 |
| propylene glycol | 10.0 |
| total | 133.5 |
| glyphosate aqueous premix | |
| glyphosate ammonium salt (42% a.e. aqueous), pH 6.3 | 500.0* |
| deionized water | 350.5 |
| silicone antifoam, Shin-etsu ™ KM-90 (10%) | 1.0 |
| total | 851.5 |
| viscosity modifying agent | |
| colloidal hydrophilic silica, Aerosil ™ COK-84 | 15.0 |

*equivalent to 210 g glyphosate a.e.

A similar composition to that of Table 13, but omitting the organic solvent (phenylxylylethane), was also prepared. Both compositions were stored at room temperature for 4 months, after which time physical stability was evaluated. The "complete" composition of Table 13 exhibited excellent physical stability, with no evidence of settling, top clearing or phase separation. By contrast, the composition lacking the organic solvent exhibited settling of the flumioxazin particles as well as separation of the emulsifying agents as a separate phase above the aqueous phase.

This provides further evidence of the superior physical stability of compositions of the invention having a barrier layer comprising an organic solvent intimately surrounding each solid particle of a water-insoluble pesticide, in this case flumioxazin.

Example 12

To verify that glyphosate-flumioxazin compositions of the invention provide earlier herbicidal symptoms and more effective control of annual dicotyledonous weeds than a commercial standard formulation of glyphosate, a greenhouse test was conducted on "inutade" (*Polygonum longisetum*) and "tsuyukusa" (*Commelina communis*). "Inutade" plants were 25–35 cm in height and "tsuyukusa" plants 30–35 cm in height when sprayed. Compositions were applied by spraying at the rates indicated, following dilution in water to provide a spray volume of 1000 l/ha. The following formulations were included in this test:

12.1. A composition of the invention containing glyphosate isopropylammonium salt, 240 g a.e./l and flumioxazin, 12 g/l (20:1 ratio), applied at 4.0 l/ha and 6.0 l/ha. This is essentially the same composition as detailed in Example 9 (Table 12).

12.2. A composition of the invention containing glyphosate isopropylammonium salt, 240 g a.e./l and flumioxazin, 18 g/l (13.3:1 ratio), applied at 4.0 l/ha and 6.0 l/ha.

12.3. A composition of the invention containing glyphosate isopropylammonium salt, 240 g a.e./l and flumioxazin, 24 g/l (10:1 ratio), applied at 4.0 l/ha and 6.0 l/ha.

Roundup® herbicide of Monsanto Company, containing glyphosate isopropylammonium salt, 360 g a.e./l, was applied at 6.0 l/ha and 10.0 l/ha as a comparative standard.

Tank-mix applications of Roundup® and flumioxazin were also made, at the same rates and ratios as provided by the compositions of the invention. Glyphosate a.e. rates in this test were 0.96 kg/ha and 1.44 kg/ha in the case of compositions of the invention and tank-mixes of Roundup® with flumioxazin, and 2.16 kg/ha and 3.60 kg/ha in the case of Roundup® alone.

Herbicidal effectiveness was recorded as percent inhibition 3, 7, 12, 20 and 27 days after treatment (DAT). Results are shown in Table 14.

TABLE 14

Greenhouse evaluation of herbicidal effectiveness of glyphosate-flumioxazin compositions of the invention

| | | % inhibition species: | | | | | | | | |
|---|---|---|---|---|---|---|---|---|---|---|
| | | inutade | | | | | tsuyukusa | | | |
| | | DAT: | | | | | | | | |
| composition | rate* | 3 | 7 | 12 | 20 | 27 | 3 | 7 | 12 | 20 | 27 |
| 12.1 | 960 + 48 | 4 | 15 | 29 | 72 | 96 | 7 | 20 | 60 | 91 | 98 |
| 12.2 | 960 + 72 | 4 | 13 | 27 | 68 | 95 | 6 | 20 | 75 | 98 | 98 |
| 12.3 | 960 + 96 | 4 | 16 | 39 | 80 | 100 | 7 | 33 | 88 | 100 | 100 |
| tank-mix | 960 + 48 | 4 | 20 | 34 | 55 | 90 | 5 | 34 | 75 | 98 | 97 |
| tank-mix | 960 + 72 | 4 | 18 | 33 | 77 | 97 | 8 | 28 | 83 | 98 | 98 |
| tank-mix | 960 + 96 | 3 | 15 | 21 | 43 | 75 | 6 | 30 | 72 | 93 | 89 |
| 12.1 | 1440 + 72 | 12 | 20 | 35 | 63 | 96 | 15 | 33 | 83 | 100 | 100 |
| 12.2 | 1440 + 108 | 16 | 29 | 63 | 85 | 100 | 14 | 39 | 88 | 100 | 100 |
| 12.3 | 1440 + 144 | 8 | 24 | 55 | 89 | 100 | 10 | 31 | 77 | 98 | 99 |
| tank-mix | 1440 + 72 | 5 | 18 | 42 | 77 | 99 | 10 | 34 | 89 | 100 | 100 |
| tank-mix | 1440 + 108 | 5 | 24 | 55 | 77 | 96 | 8 | 39 | 84 | 100 | 100 |
| tank-mix | 1440 + 144 | 4 | 22 | 35 | 67 | 96 | 7 | 37 | 78 | 99 | 100 |
| Roundup ® | 2160 + 0 | 0 | 0 | 1 | 45 | 70 | 0 | 0 | 6 | 50 | 62 |
| Roundup ® | 3600 + 0 | 0 | 0 | 6 | 75 | 98 | 0 | 0 | 4 | 43 | 76 |

*glyphosate g a.e./ha + flumioxazin g/ha

The herbicidal effectiveness benefits of glyphosate+flumioxazin over glyphosate alone, as seen in tank-mix applications, are at least as great when applied in the form of a package-mix composition of the invention. Indeed, in some instances it appears that effectiveness is greater with the package-mix composition than with the corresponding tank-mix. This is especially true at the higher flumioxazin rates, perhaps as a result of antagonism by flumioxazin on glyphosate effectiveness seen with the tank-mix being less pronounced in the package-mix.

The preceding description of specific embodiments of the present invention is not intended to be a complete list of every possible embodiment of the invention. Persons skilled in this field will recognize that modifications can be made to the specific embodiments described here that remain within the scope of the invention.

What is claimed is:

1. A concentrate composition comprising a continuous aqueous phase having dissolved therein a water-soluble pesticide or plant growth regulator, and having suspended therein solid particles of a substantially water-insoluble pesticide or plant growth regulator, said solid particles, individually or plurally, being intimately surrounded by a barrier layer comprising one or more water-immiscible organic solvents in the absence of non-ionic or anionic emulsifying agents having a hydrophile-lipophile balance not greater than about 15 and wherein the pesticides or plant growth regulators of the composition consist of said water-soluble pesticides or plant growth regulators and said water-insoluble pesticides or plant growth regulators that are no more than sparingly soluble in said organic solvents.

2. The composition of claim 1, further comprising a viscosity modifying agent dispersed in the aqueous phase.

3. The composition of claim 2, wherein the viscosity modifying agent is colloidal hydrophilic silica.

4. The composition of claim 1 wherein the water-soluble active ingredient is a pesticide or plant growth regulator selected from acephate, acifluorfen, acrolein, amitrole, asulam, benazolin, bentazon, bialaphos, borax, bromacil, bromoxynil, butoxycarboxim, sec-butylamine, calcium polysulfide, cartap, chloramben, chlormequat, chloroacetic acid, chlorphonium, clofencet, clopyralid, cloxyfonac, copper sulfate, cyanamide, 2,4-D, 2,4-DB, dalapon, daminozide, dicamba, dichlorprop, diclofop, dicrotophos, difenzoquat, dikegulac, diquat, endothall, ethephon, fenac, fenoxaprop, flamprop, fluazifop, fluoroglycofen, flupropanate, fomesafen, formetanate, fosamine, fosetyl, glufosinate, glyphosate, guazatine, haloxyfop, hydrogen cyanide, hydroxyquinoline sulfate, imazameth, imazamethabenz, imazamox, imazapic, imazapyr, imazaquin, imazethapyr, iminoctadine, ioxynil, kasugamycin, MCPA, MCPB, mecoprop, mepiquat, mercuric chloride, metam, methamidophos, methomyl, methylarsonic acid, mevinphos, monocrotophos, nabam, naptalam, nicotine, nitenpyram, nonanoic acid, omethoate, oxamyl, oxydemeton-methyl, paraquat, phosphamidon, picloram, polyoxin B, propamocarb, sulfamic acid, 2,3,6-TBA, thiocyclam, trichlorfon, trichloroacetic acid, triclopyr, validamycin, vamidothion, and agriculturally acceptable salts thereof.

5. The composition of claim 1 wherein the substantially water-insoluble active ingredient is a pesticide or plant growth regulator selected from abamectin, aclonifen, acrinathrin, amitraz, atrazine, azadirachtin, azamethiphos, azinphos-methyl, azocyclotin, azoxystrobin, benalaxyl, benomyl, bensulfuron-methyl, bensultap, benzofenap, 6-benzylaminopurine, bifenox, bifenthrin, bitertanol, bromobutide, bromofenoxim, bromopropylate, bromuconazole, buprofezin, captafol, captan, carbendazim, chinomethionat, chlomethoxyfen, chlorbromuron, chlorfenapyr, chlorfenson, chlorfluazuron, chlorimuron-ethyl, chlornitrofen, chlorothalonil, chlorotoluron, chlorthal-dimethyl, chlozolinate, clofentezene, clomeprop, coumaphos, cyclanilide, cyfluthrin, β-cyfluthrin, cypermethrin, α-cypermethrin, θ-cypermethrin, cyprodinil, daimuron, DDT, deltamethrin, desmedipham, diafenthiuron, dichlobenil, dichlofluanid, dichlorofen, diclomezine, dicloran, dicofol, diethofencarb, diflubenzuron, diflufenican, dimefuiron, dimethomorph, diniconazole, dinitramine, dithianon, diuron, endosulfan, epoxiconazole, esfenvalerate, ethametsulfuron-methyl, etoxazole, famoxadone, fenarimol, fenazaquin, fenbuconazole, fenbutatin oxide, fenfuram, fenoxaprop-ethyl, fenoxycarb, fenpiclonil, fenpyroximate, fentin, fipronil, flamprop-methyl, flazasulfuron, fluazinam, fluazuron, flucycloxuron, fludioxonil, flufenoxuron, flumetralin, flumetsulam, flumiclorac-pentyl, flumioxazin, fluoroimide, flupoxam, fluquinconazole, fluridone, flurtamone, flusulfamide, flutolanil, folpet, forchlorfenuron, halofenozide, γ-HCH, hexachlorobenzene, hexaconazole, hexaflumuron, hexythiazox, hydramethylnon, imibenconazole, inabenfide, ipconazole, iprodione, isoproturon, isoxaben, isoxapyrifop, kresoxim-methyl, lactofen, lenacil, linuron, lufenuron, mancozeb, maneb, mefenacet, mepanipyrim, mepronil, metconazole, methabenzthiazuron, methiocarb, methoxychlor, metiram, metobenzuron, milbemectin, 2-(1-naphthyl)acetamide, naproanilide, neburon, nickel bis(dimethyldithiocarbamate), norflurazon, novaluron, nuarimol, oryzalin, oxadiazon, oxine copper, oxolinic acid, oxyfluorfen, paclobutrazol, pencycuron, pentachlorophenol, phenmedipham, N-phenylphthalamic acid, phthalide, procymidone, prodiamine, prometryn, propazine, propineb, propyzamide, pyrazolynate, pyrazosulfuron-ethyl, pyributicarb, pyridaben, quinclorac, quintozene, quizalofop-ethyl, resmethrin, rimsulfuron, rotenone, siduron, simazine, sulfluramid, sulfur, tebuconazole, tebufenozide, tebufenpyrad, tebupirimfos, tecloftalam, tecnazene, teflubenzuron, terbuthylazine, terbutryn, tetrachlorvinphos, tetradifon, tetramethrin, thiazopyr, thidiazuron, thifluzamide, thiodicarb, thiophanate-methyl, thiram, tolclofos-methyl, tolylfluanid, tralkoxydim, tralomethrin, triadimefon, triadimenol, triazoxide, trietazine, triflumuron, triforine, trimethacarb, triticonazole, uniconazole, vinclozolin, zineb and ziram.

6. The composition of claim 1 wherein the substantially water-insoluble active ingredient has a melting point of not less than about 75° C.

7. The composition of claim 1 wherein the water-soluble pesticide or plant growth regulator is a salt of glyphosate selected from the diammonium, monosodium, monopotaosium, monoaminonium, mono (dimethylammonium, mono(ethanolammonium), mono ((isopropylammonium) and mono(trimethylsulfonium) salts.

8. The composition of claim 1 wherein the water-soluble pesticide or plant growth regulator is a herbicide or an agriculturally acceptable salt thereof.

9. The composition of claim 8 wherein the water-soluble active ingredient is a salt of a compound selected from glyphosate, glufosinate, imazameth, imazamethabenz, imazamox, imazapic, imazapyr, imazaquin and imazethapyr.

10. The composition of claim 9 wherein the salt comprises counterions selected from sodium, potassium, ammonium, $C_{1-16}$ organic ammonium and $C_{1-16}$ organic sulfonium cations.

11. A method of eliciting a biological effect in a plant comprising diluting a composition of claim 1 in a suitable volume of water to form a diluted composition, and applying a biologically effective amount of the diluted composition to a locus from which active ingredients contained in the composition can enter the plant.

12. A herbicidal concentrate composition comprising a continuous aqueous phase having dissolved therein an agriculturally acceptable water-soluble salt of glyphosate, having suspended therein solid particles of flumioxazin and having dispersed therein colloidal hydrophilic silica; said solid particles of flumioxazin, individually or plurally, being intimately surrounded by a barrier layer comprising a water-immiscible organic solvent and an emulsifying agent, said emulsifying agent having a hydrophile-lipophile balance not greater than about 15.

13. The composition of claim 12 wherein the barrier layer comprises phenylxylylethane and an anionic or nonionic emulsifying agent, said emulsifying agent having a hydrophile-lipophile balance not greater than about 11.

14. The composition of claim 12 wherein the glyphosate is present at an acid equivalent concentration of about 36 to about 480 g/l.

15. The composition of claim 12 wherein the glyphosate is present at an acid equivalent concentration of about 180 to about 360 g/l.

16. The composition of claim 12 wherein the weight ratio of glyphosate acid equivalent to flumioxazin is about 100:1 to about 5:1.

17. The composition of claim 12 wherein the weight ratio of glyphosate acid equivalent to flumioxazin is about 30:1 to about 10:1.

18. A composition according to claim 12 that exhibits enhanced resistance to settling of solid particles by comparison with an otherwise similar composition lacking only the organic solvent.

19. A composition according to claim 12 that exhibits enhanced resistance to chemical degradation of the flumioxazin by comparison with an otherwise similar composition lacking only the barrier layer.

20. A herbicidal method comprising diluting a composition of claim 12 in a suitable volume of water to form a diluted composition, and applying a herbicidally effective amount of the diluted composition to foliage of plants by spraying.

21. A process for preparing a composition of claim 1, the process comprising
  (a) adding to a first vessel a particulate solid water-insoluble pesticide or plant growth regulator and one or more water-immiscible organic solvents in the absence of non-ionic or anionic emulsifying agents having a hydrophile-lipophile balance not greater than about 15 and mixing to form a homogeneous suspension premix;
  (b) adding to a second vessel a water-soluble pesticide or plant growth regulator and water to form an aqueous premix;
  (c) adding, under agitation, a first portion of the aqueous premix to the suspension premix to form a homogeneous high-viscosity mixture; and
  (d) adding to the high-viscosity mixture, under continuing agitation, a second portion of the aqueous premix to form the coposition.

22. The process of claim 21, further comprising adding a viscosity modifying agent during step (c).

23. A concentrate composition comprising a continuous aqueous phase having dissolved therein a water-soluble active ingredient that is a pesticide or plant growth regulator, and having suspended therein solid particles of a substantially water-insoluble active ingredient that is a pesticide or a plant growth regulator; said solid particles, individually or plurally, being intimately surrounded by a barrier layer comprising one or more water-immiscible organic solvents and one or more emulsifying agents, said emulsifying agents having a hydrophile-lipophile balance not greater than about 15, and wherein the pesticides or plant growth regulators of the composition consist of said water-soluble pesticides or plant growth regulators and said water-insoluble pesticides or plant growth regulators that are no more than sparingly soluble in said organic solvents.

24. A method of eliciting a biological effect in a plant comprising diluting a composition of claim 23 in a suitable volume of water to form a diluted composition, and applying a biologically effective amount of the diluted composition to a locus from which active ingredients contained in the composition can enter the plant.

25. The composition of claim 23, further comprising a viscosity modifying agent dispersed in the aqueous phase.

26. The composition of claim 25, wherein the viscosity modifying agent is colloidal hydrophilic silica.

27. The composition of claim 23 wherein the water-soluble active ingredient is a pesticide or plant growth regulator selected from acephate, acifluorfen, acrolein, amitrole, asulam, benazolin, bentazon, bialaphos, borax, bromacil, bromoxynil, butoxycarboxim, sec-butylamine, calcium polysulfide, cartap, chloramben, chlormequat, chloroacetic acid, chlorphonium, clofencet, clopyralid, cloxyfonac, copper sulfate, cyanamide, 2,4-D, 2,4-DB, dalapon, daminozide, dicamba, dichlorprop, diclofop, dicrotophos, difenzoquat, dikegulac, diquat, endothall, ethephon, fenac, fenoxaprop, flamprop, fluazifop, fluoroglycofen, flupropanate, fomesafen, formetanate, fosamine, fosetyl, glufosinate, glyphosate, guazatine, haloxyfop, hydrogen cyanide, hydroxyquinoline sulfate, imazameth, imazamethabenz, imazamox, imazapic, imazapyr, imazaquin, imazethapyr, iminoctadine, ioxynil, kasugamycin, MCPA, MCPB, mecoprop, mepiquat, mercuric chloride, metam, methamidophos, methomyl, methylarsonic acid, mevinphos, monocrotophos, nabam, naptalam, nicotine, nitenpyram, nonanoic acid, omethoate, oxamyl, oxydemeton-methyl, paraquat, phosphamidon, picloram, polyoxin B, propamocarb, sulfamic acid, 2,3,6-TBA, thiocyclam, trichlorfon, trichloroacetic acid, triclopyr, validamycin, vamidothion, and agriculturally acceptable salts thereof.

28. The composition of claim 23 wherein the substantially water-insoluble active ingredient is a pesticide or plant growth regulator selected from abamectin, aclonifen, acrinathrin, amitraz, atrazine, azadirachtin, azamethiphos, azinphos-methyl, azocyclotin, azoxystrobin, benalaxyl, benomyl, bensulfuron-methyl, bensultap, benzofenap, 6-benzylaminopurine, bifenox, bifenthrin, bitertanol, bromobutide, bromofenoxim, bromopropylate, bromuconazole, buprofezin, captafol, captan, carbendazim, chinomethionat, chlomethoxyfen, chlorbromuron, chlorfenapyr, chlorfenson, chlorfluazuron, chlorimuron-ethyl, chlornitrofen, chlorothalonil, chlorotoluron, chlorthal-dimethyl, chlozolinate, clofentezene, clomeprop, coumaphos, cyclanilide, cyfluthrin, β-cyfluthrin, cypermethrin, α-cypermethrin, θ-cypermethrin, cyprodinil, daimuron, DDT, deltamethrin, desmedipham, diafenthiuron, dichlobenil, dichlofluanid, dichlorofen, diclomezine, dicloran, dicofol, diethofencarb, diflubenzuron, diflufenican, dimefuron, dimethomorph, diniconazole, dinitramine, dithianon, diuron, endosulfan, epoxiconazole, esfenvalerate, ethametsulfuron-methyl, etoxazole, famoxadone, fenarimol, fenazaquin, fenbuconazole, fenbutatin oxide, fenfuram, fenoxaprop-ethyl, fenoxycarb, fenpiclonil, fenpyroximate, fentin, fipronil, flamprop-methyl, flazasulfuron, fluazinam, fluazuron, flucycloxuron, fludioxonil, flufenoxuron, flumetralin, flumetsulam, flumiclorac-pentyl, flumioxazin, fluoroimide, flupoxam, fluquinconazole, fluridone, flurtamone, flusulfamide, flutolanil, folpet, forchlorfenuron, halofenozide, γ-HCH, hexachlorobenzene, hexaconazole, hexaflumuron, hexythiazox, hydramethylnon, imibenconazole, inabenfide, ipconazole, iprodione, isoproturon, isoxaben, isoxapyrifop, kresoxim-methyl, lactofen, lenacil, linuron, lufenuron, mancozeb, maneb, mefenacet, mepanipyrim, mepronil, metconazole, methabenzthiazuron, methiocarb, methoxychlor, metiram, metobenzuron, milbemectin, 2-(1-naphthyl)acetamide, naproanilide, neburon, nickel bis(dimethyldithiocarbamate), norflurazon, novaluron, nuarimol, oryzalin, oxadiazon, oxine copper, oxolinic acid, oxyfluorfen, paclobutrazol, pencycuron, pentachlorophenol, phenmedipham, N-phenylphthalamic acid, phthalide, procymidone, prodiamine, prometryn, propazine, propineb, propyzamide, pyrazolynate, pyrazosulfuron-ethyl, pyributicarb, pyridaben, quinclorac, quintozene, quizalofop-ethyl, resmethrin, rimsulfuron, rotenone, siduron, simazine, sulfluramid, sulfur, tebuconazole, tebufenozide, tebufenpyrad, tebupirimfos, tecloftalam, tecnazene, teflubenzuron, terbuthylazine, terbutryn, tetrachlorvinphos, tetradifon, tetramethrin, thiazopyr, thidiazuron, thifluzamide, thiodicarb, thiophanate-methyl, thiram, tolclofos-methyl, tolylfluanid, tralkoxydim, tralomethrin, triadimefon, triadimenol, triazoxide, trietazine, triflumuron, triforine, trimethacarb, triticonazole, uniconazole, vinclozolin, zineb and ziram.

29. The composition of claim 23 wherein the substantially water-insoluble active ingredient has a melting point of not less than about 75° C.

30. The composition of claim 23 wherein the water-soluble active ingredient is a herbicide or an agriculturally acceptable salt thereof.

31. The composition of claim 30 wherein the water-soluble active ingredient is a salt of a compound selected from glyphosate, glufosinate, imazameth, imazamethabenz, imazamox, imazapic, imazapyr, imazaquin and imazethapyr.

32. The composition of claim 31 wherein the salt comprises counterions selected from sodium, potassium, ammonium, $C_{1-16}$ organic ammonium and $C_{1-16}$ organic sulfonium cations.

33. The composition of claim 23 wherein the water-soluble active ingredient is a salt of glyphosate selected from the diammonium, monosodium, monopotassium, monoammonium, mono(dimethylammonium), mono (ethanolammonium), mono(isopropylammonium) and mono(trimethylsulfonium) salts.

34. A herbicidal concentrate composition comprising a continuous aqueous phase having dissolved therein a agriculturally acceptable water-soluble salt of glyphosate, having suspended therein solid particles of flumioxazin and having dispersed therein colloidal hydrophilic silica; said solid particles of flumioxazin, individually or plurally, being intimately surrounded by a barrier layer comprising one or more water-immiscible organic solvents in the absence of nonionic or anionic emulsifying agents having a hydrophile-lipophile balance not greater than about 15.

35. The composition of claim 34 wherein the glyphosate is present at an acid equivalent concentration of about 36 to about 360 g/l.

36. The composition of claim 34 wherein the glyphosate is present at an acid equivalent concentration of about 180 to about 360 g/l.

37. The composition of claim 34 wherein the ratio of glyphosate acid equivalent to flumioxazin is about 100:1 to about 5:1.

38. The composition of claim 34 wherein the ratio of glyphosate acid equivalent to flumioxazin is about 30:1 to about 10:1.

39. A composition according to claim 34 that exhibits enhanced resistance to settling of solid particles by comparison with an otherwise similar composition lacking only the organic solvent.

40. A composition according to claim 34 that exhibits enhanced resistance to chemical degradation of the flumioxazin by comparison with an otherwise similar composition lacking only the barrier layer.

41. A herbicidal method comprising diluting a composition of claim 34 in a suitable volume of water to form a diluted composition, and applying a herbicidally effective amount of the diluted composition to foliage of plants by spraying.

42. A process for preparing a composition of claim 23, the process comprising (a) adding to a first vessel a particulate solid water-insoluble pesticide or plant growth regulator and one or more water-immiscible organic solvents and one or more emulsifying agents, said emulsifying agents having a hydrophile-lipophile balance not greater than about 15 and mixing to form a homogeneous suspension premix;

(b) adding to a second vessel a water-soluble pesticide or plant growth regulator and water to form an aqueous premix;

(c) adding, under agitation, a first portion of the aqueous premix to the suspension premix to form a homogeneous high-viscosity mixture; and (d) adding to the high-viscosity mixture, under continuing agitation, a second portion of the aqueous premix to form the composition.

43. The process of claim 42 further comprising adding a viscosity modifying agent during step (c).

* * * * *